United States Patent [19]

Strepparola et al.

[11] Patent Number: 5,210,188

[45] Date of Patent: May 11, 1993

[54] DYESTUFFS FOR PERFLUOROPOLYOXYALKYLENES AND COMPOSITIONS BASED ON PERFLUOROPOLYOXYALKYLENES CONTAINING SUCH DYESTUFFS

[75] Inventors: Ezio Strepparola, Treviglio; Piero Gavezotti; Giovanni Gavazzi, both of Milan, all of Italy

[73] Assignee: Ausimont S.p.A., Milan, Italy

[21] Appl. No.: 833,524

[22] Filed: Feb. 11, 1992

[30] Foreign Application Priority Data

Feb. 15, 1991 [IT] Italy .............. 91 A/000395

[51] Int. Cl.$^5$ .......... C09B 1/36; C09B 11/12; C09B 29/00; C09B 17/00
[52] U.S. Cl. .................. 534/728; 534/849; 534/858; 534/859; 544/348; 552/113; 552/114; 8/636; 8/662; 8/675; 8/689; 546/103; 546/153
[58] Field of Search ............ 534/728, 849, 855, 859; 544/348; 552/113, 114; 554/248; 8/636, 662, 675, 689

[56] References Cited

U.S. PATENT DOCUMENTS

| 2,436,100 | 2/1948 | Dickey | 534/849 X |
|---|---|---|---|
| 2,516,302 | 7/1950 | Dickey | 534/858 X |
| 2,516,303 | 7/1950 | Dickey | 534/858 X |
| 2,768,160 | 10/1956 | Dickey et al. | 534/858 X |
| 3,242,218 | 3/1966 | Miller | 568/683 X |
| 3,665,041 | 5/1972 | Sianesi et al. | 568/683 X |
| 3,715,378 | 2/1973 | Sianesi et al. | 562/849 X |
| 3,810,874 | 5/1974 | Mitsch et al. | 568/683 X |
| 4,049,375 | 9/1977 | Pechmeze | 534/859 X |
| 4,267,238 | 5/1981 | Chernega | 428/422 |
| 4,268,556 | 5/1981 | Pedrotty | 428/65 |
| 4,523,039 | 6/1985 | Lagow et al. | 568/615 |
| 4,721,795 | 1/1988 | Caporiccio et al. | 549/445 |
| 4,808,472 | 2/1989 | Caporiccio et al. | 528/335 |

FOREIGN PATENT DOCUMENTS

| 0148482 | 7/1985 | European Pat. Off. | 568/683 |
| 323060 | 7/1989 | European Pat. Off. | 534/573 |
| 361346 | 4/1990 | European Pat. Off. | 568/683 |
| 2106375 | 5/1972 | France | 568/683 |
| WO87/00538 | 1/1987 | PCT Int'l Appl. | 568/615 |

OTHER PUBLICATIONS

Cabut et al., Chemical Abstracts, vol. 86, #'s 141618v and 141619w (1977).
Gandel'man et al., Chemical Abstracts, vol. 82, #172578d (1975).
Kiji et al., Chemical Abstracts, vol. 106, #50236j (1987).
Makino et al., Chemical Abstracts, vol. 105, #235764c (1986).
Whittaker, Chemical Abstracts, vol. 96, #144468p (1982).
J. Am. Chem. Soc. 1985, 107, 1197–1201, "Synthesis of Perfluoropolyethers via Hydrocarbon Polyesters: A New General Method", Persico et al.

Primary Examiner—Floyd D. Higel
Attorney, Agent, or Firm—Bryan Cave

[57] ABSTRACT

1. Dyestuffs for cyclic or straight polyfluoropolyoxyalkylenes, of general formula:

$$Q[B-(A)_s]_t \qquad (III)$$

or $$[(Q)_s-B]_2A \qquad (IV)$$

where:
Q=an organic group containing a chromophore group, free from free or salified sulphonic and/or carboxylic groups, and/or sulphon-amidic groups;
A=a perfluorooxyalkylene chain, which is monovalent in formula (II) and divalent in formula (III);
B=an organic at least divalent group;
s, t=1 or 2, respectively.

2. Compositions comprising cyclic or straight polyfluoropolyoxyalkylenes and at least a dyestuff of formula (III) or (IV) dissolved therein.

3 Claims, No Drawings

DYESTUFFS FOR PERFLUOROPOLYOXYALKYLENES AND COMPOSITIONS BASED ON PERFLUOROPOLYOXYALKYLENES CONTAINING SUCH DYESTUFFS

The present invention relates to dyestuffs for compounds having polyfluoropolyoxyalkylene structure and to compositions based on such compounds, containing said dyestuffs.

Compounds endowed with poly- or perfluoropolyoxyalkylene structure (from time to time referred to as polyperfluoroalkylene oxide, fluorocarbon ethers or also simply perfluoropolyethers) are known in the art. They can be straight or cyclic and can have, respectively, the general formula:

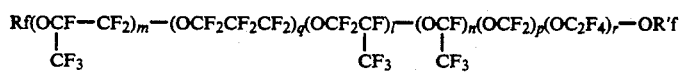

or

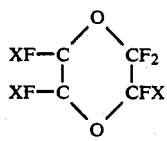

where X=F, CF$_3$, Rf and R'f, like or different from each other, are perfluoroalkyl radicals containing 1 to 3 carbon atoms, l, m, n, p, q, r are numbers ranging from 0 to 50, extremes included, the sum l+m+n+p+q+r being at least 2, and where the perfluorooxyalkylene units are randomnly distributed along the perfluoropolyoxyalkylene chain, or Rf and R'f, like or different from each other, are groups of formula —CFXL, where X=F, CF$_3$, and L is a functional organic radical having one of the following formulae:

a) —COR$_1$, in which R$_1$ can be a radical —OR$_2$ or —NR$_2$R$_3$, where R$_2$=H or an alkyl containing 1 to 16 carbon atoms; R$_3$ can be equal to R$_2$, or it can be a radical selected from —CH$_2$CH$_2$OH; —(CH$_2$CH$_2$O)$_n$H with n ranging from 2 to 6, extremes included; —(CH$_2$)$_3$Si(OR$_8$)$_3$ where R$_8$=—CH$_3$ or —C$_2$H$_5$; —CH$_2$—CH=CH$_2$; phenyl; or

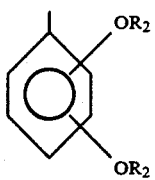

or a heterocyclic radical.

b) —CH$_2$R$_4$, in which R$_4$ can be a radical —OR$_5$ or —NR$_5$R$_6$, where R$_5$ and R$_6$, like or different from each other, can be H, —CH$_2$CH$_2$OH;

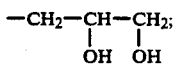

—(CH$_2$CH$_2$O)$_n$H with n ranging from 2 to 6, extremes included;

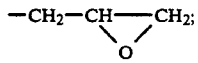

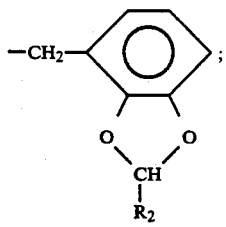

$CH_2CH_2CH_2Si(OR_8)_3$;

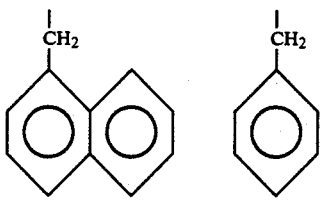

or a heterocyclic radical, where R$_2$ and R$_8$ are the same as defined under the preceding point (a).

Their average molecular weight generally ranges from 500 to 15,000 in the case of straight products, and from 232 to 332 in the case of cyclic products.

The properties of the polyfluoropolyoxyalkylene products have stimulated a considerable research activity in the field of their possible applications.

Generally, in the above-mentioned molecular weight ranges, they appear in the form of transparent colorless liquids in a wide temperature range.

Because of their low affinity for the non-fluorinated organic compounds, it was not possible so far to obtain colored compositions of such products by mixing them with conventional dyestuffs, at least in the cases in which the perfluoropolyoxyalkylene does not possess functional groups or, although it possesses such groups, it has a high molecular weight, generally not lower than 1,500.

An object of the present invention is represented by dyestuffs which are soluble in polyfluoropolyoxyalkylenes and therefore are suitable for preparing, by admixing with the polyfluoropolyoxyalkylenes, colored compositions of the latter.

A further object of the present invention is represented by such compositions.

The dyestuffs forming an object of the present invention are comprised in one of the following general formulas:

$$Q[B-(A)_s]_t \quad (III)$$

or $$[(Q)_s-B]_2A \quad (IV)$$

In the case of the dyestuffs of formula (III):

Q=organic group, free from sulphonic and/or carboxylic groups, either free or salified with alkaline metals, and/or from sulphonamidic groups, such organic group carrying a chromophore group and belonging to one of the dyestuff classes as are defined hereinafter:

A=chains having a perfluorooxyalkylene structure comprising perfluorooxyalkylene units of formula:

$$(CFO), \quad (CF_2CF_2O), \quad (CF_2CF_2CF_2O),$$
$$\phantom{XXXX}X$$

$$(CF-CF_2O), \quad (CF_2-CF-O)$$
$$\phantom{XXX}CF_3 \phantom{XXXXXX} CF_3$$

(where X=F or CF$_3$) randomly arranged in the chain and having general formula:

$$(F)_k - C_zF_{2z}O(CFO)_m(C_2F_4O)_n(C_3F_6O)_pC_zCF_{2z} - \quad (V)$$
$$\phantom{XXXXXXXXX}X$$

where X=F, CF$_3$ and where the units in the chains and in the end groups can have all the above-indicated isomeric structures, k=1; z=number from 1 to 3, extremes included; m, n, p are integers ranging from 0 to 50, extremes included, the sum of which being at least equal to 2. The average molecular weight of A ranges from 500 to 15,000.

B=an at least divalent organic group which links the dyeing group Q to the perfluoropolyoxyalkylene chain A, so forming a Q-B-A sequence. As an example, B can have formula:

—O—CH$_2$—

—(OCH$_2$CH$_2$)$_n$OCH$_2$—

—CH$_2$OCH$_2$—

—S—CH$_2$CH$_2$OCH$_2$—

—CH$_2$OCH$_2$OCH$_2$—

—CH$_2$OCH$_2$CH$_2$OCH$_2$—

$$-CH\begin{matrix}\diagup OCH_2-\\ \diagdown OR_q\end{matrix}$$

(R$_q$ = an alkyl containing 1 to 3 carbon atoms)

—N—C—; —N(CH$_2$)$_r$—N—C; —N(CH$_2$)$_r$—O—C—;
| ‖ | | ‖ | ‖
H O R$_{10}$ H O R$_{10}$ O $$-O-\underset{\underset{O}{\|}}{C}-; \quad -N\begin{matrix}\diagup CH_2CH_2-N-C-\\ \phantom{X}\phantom{X}| \phantom{X}\|\\ \phantom{X}\phantom{X}R_{10}\, O\\ \diagdown CH_2CH_2-N-C-\\ \phantom{X}\phantom{X}| \phantom{X}\|\\ \phantom{X}\phantom{X}R_{10}\, O\end{matrix}$$

-continued

—NCH$_2$CH$_2$OCH$_2$— —N—CH$_2$— (R$_{10}$ = H or an
|  | alkyl containing 1 to
H R$_{10}$ 3 carbon atoms);

—O—C— (in this case, the group represented by the
‖ dyestuff possesses a positive charge (Q$^+$) and
O is bound to the —O—C— group through
‖
O a ionic bond.

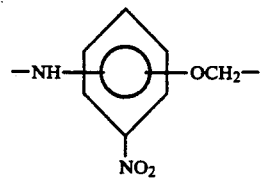

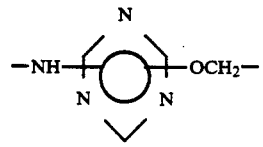

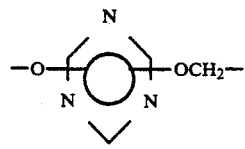

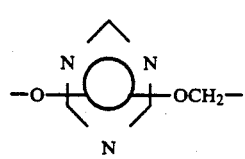

t=1 or 2;

s=1 or 2;

r=1, 2, 3;

n=2 to 6, extremes included.

In the case of the dyestuffs of formula (IV), A is a chain having a perfluoropolyoxyalkylene structure similar to the one of formula (V), where, however, k is 0; s is 1 or 2; B is the same as defined in formula (III), as a bridge between Q and A in the Q-B-A sequences.

In both formulae (III) and (IV), group Q belongs to one of the following classes of dyestuffs:

1. Azo dyestuffs, characterized by the presence, in the molecule, of at least a -N=N- group as a chromophore group, and in particular the sub-classes of the monoazo, diazo and triazo dyestuffs, optionally containing hydroxylic and/or aminic auxochrome groups.

As an example, the dyestuffs as per the following Color Index numbers are cited: 11,000–11,160; 11,180–11,335; 11,350–11,435; 11,825; 20,000–20,010; 21,000–21,060; 21,230–21,270; 26.000–26,050; 26,075–26,150.

2. Stilbene dyestuffs, out of which there are cited, as an example, the ones mentioned under the C.I. Nos. 40,500–40,510.

3. Diphenylmethane dyestuffs, characterized by the presence, in the molecule, of chromophore group C=NH and of chromogen group

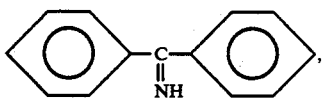

As an example, the dyestuffs mentioned under the C.I. Nos. 41,000, 41,000:1, 41,000:2 and 41,005 are cited.

4. Triarylmethane dyestuffs (characterized by the chromophore group

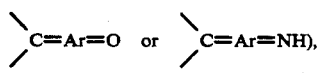

in which two aryl groups bound to the methane carbon atoms complete the chromogen group, and comprising two or three auxochrome groups usually on the aryl groups and in para position with respect to the methane carbon atom.

As an example there are cited the dyestuffs indicated under the following C.I. numbers: 42,000, - - - 42,025, 42,030, 42,035, 42,036, 42,037, 42,040, 42,130, 42,140, 42,500–42,520, 42,555, 42,557, 42,563, 42,590, 42,595, 42,600, 42,705, 42,760, 42,785, 44,000, 44,045, 44,060

5. Xanthen dyestuffs, in the classes of the aminic, hydroxy and hydroxyaminic derivatives, characterized by the chromophore groups

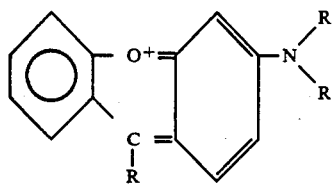

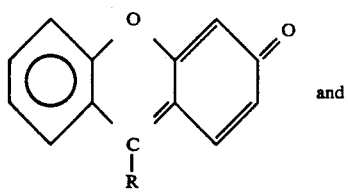

and

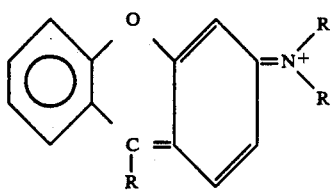

where R=H, alkyl, aryl.

As an example there are cited the Pyronines (C.I. 45,000–45,020), the Succineines (45,050), the Rosamines (C.I. 45,090–45,105), the Rhodoles (C.I. 45,310–45,315), the Anthrahydroxyphthaleins (C.I. 45,500–45,510).

6. Acridine dyestuffs, characterized by the chromophore group:

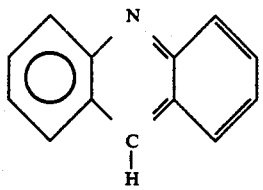

containing auxochrome groups in the aryl in para position to the carbon atom of the methane radical.

As an example there are cited the dyestuffs indicated under the C.I. Nos. 46,000–46.080.

7. Quinoline dyestuffs, characterized by the chromophore group

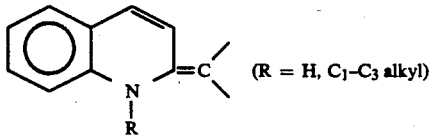

(R = H, $C_1$–$C_3$ alkyl)

examples of which are the dyestuffs cited under the C.I. Nos. 47,025 and 47,040.

8. Methine and polymethine dyestuffs, characterized by a chromophore group consisting of a conjugated chain of carbon atoms, which binds, at the ends, quinoline, benzothiazole and trimethylindole nuclei.

As an example there are cited the dyestuffs indicated under the C.I. Nos. 48,010–48,013; 48.015–48,040; 48,060–48,080.

9. Indamine and indophenol dyestuffs, characterized by the chromophore group:

with aminic and hydroxylic groups as auxochromes, examples of which are the dyestuffs cited under the C.I. Nos. 49,400–49,410.

10. Azinic dyestuffs, characterized by the chromophore group

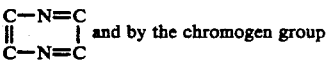

and by the chromogen group

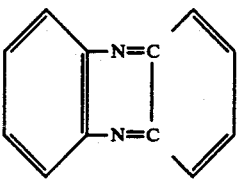

with auxochrome groups in meta position to the nitrogen atom, and to which there belong the classes of the Quinoxalines (C.I. 50,000), Eurodines (C.I. 50,030–50,045), Aposafranines in the sub-classes of the Phenylaposafranines (C.I. 50,050–50,055), Rosaindulines (C.I. 50,080), Isorosindulines (C.I. 50,150, 50,155, 50,160, 50,165), and furthermore the classes of the Safranines in the sub-classes of the Phenylsafranines (C.I. 50,200, 50,225–50,270), Benzophenylsafranines (C.I.

50,305-50,306) and Dibenzophenylsafranines (C.I. 50,370-30,375), and lastly the classes of the Indulines and Nigrosines (C.I. 50,400-50,410).

11. Oxazine dyestuffs, characterized by the chromophore group

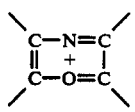

in the classes of the mono-oxazines (C.I. 51,000-51,025; 51,175-51,215).

12. Thiazine dyestuffs, characterized by the chromophore group

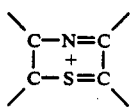

out of which, as an example, the dyestuffs indicated with the C.I. Nos. 52,000-52,030 are cited.

13. Anthraquinone dyestuffs, characterized by at least a carbonyl group as a chromophore group. Such dyestuffs comprise both the ones not containing condensed heterocyclic groups and the ones containing such groups. In this connection there are cited, as an example, the dyestuffs containing one or more aminic groups (C.I. Nos. 60,505, 60,507, 60,710, 60,715, 60,725, 60,880, 61,100, 61,105, 61,107, 64,500), as well the dyestuffs not containing aminic groups (C.I. No. 58,000).

The dyestuffs which are the object of the present invention can be prepared by reacting a dyestuff of formula Q-(Z)$_K$ with a compound having a perfluoropolyoxyalkylene structure of formula A—(Y)$_K$, where:

K = 1,2;

Q and A are the same as defined hereinbefore, while Z can be a —OH, —NHR, Cl, Br, —NR$_1$R$_2$, —CH$_2$OH, —CHO, —CH$_2$X (where X=Cl, Br) group, an aromatic group having 5-6 carbon atoms, substituted by chlorine or fluorine atoms and nitro groups in ortho and para position to one another, which can contain in the ring up to 3 heteroatoms such as N, S, O (for example a triazinic group) and having reactive groups such as —OH, —NHR, F, Cl, Br, —NR$_1$R$_2$, —CH$_2$OH, —CHO, —CH$_2$X (wherein R, R$_1$ and R$_2$ are alkyls containing 1 to 3 carbon atoms), and Y can be a group —COF, —COCl, —CH$_2$OH, —CH$_2$OCH$_2$CH$_2$SH, —CH$_2$OCH$_2$CH$_2$OH, —CH$_2$OCH$_2$CH$_2$Cl, —CH$_2$NH$_2$, —CH$_2$OCH$_2$CH$_2$NH$_2$, —COOH, —COOR (where R is the same as defined hereinbefore).

Such preparation can be effected by means of condensation reaction, etherification reaction, esterification reaction or nucleophilic substitution reaction in which movable halogen atoms are substituted by alcoholic and/or aminic groups, or by means of salification reactions, after formation of free bases, according to the conventional techniques of the organic chemistry.

The dyestuffs of formula Q—(Z)$_K$, if the Z group is not already present in the molecule of the dyestuff as such, can be obtained by the conventional methods of the organic chemistry, by introducing such group into the dyestuff molecule by means of usual condensation, halogenation, amination and nucleophilic substitution reactions.

The polyfluoropolyoxyalkylenes to which the dyestuffs of formula (III) or (IV) are added in order to obtain the compositions of the invention have the general structure which is defined in the previously illustrated formulas (I) and (II).

Said polyfluoropolyoxyalkylenes are known in the art. In particular, the polyfluoropolyoxyalkylenes containing end groups consisting of functional CFXL groups can be prepared according to the methods described in the U.S. Pat. Nos. 3,242,218, 3,665,041, 3,715,378, 4,268,556, 4,267,238 and in Italian patent application No. 21481 A/84 and in U.S. Pat. No. 3,810,874.

In particular, such polyfluoropolyoxyalkylenes can belong to at least one of the following classes:

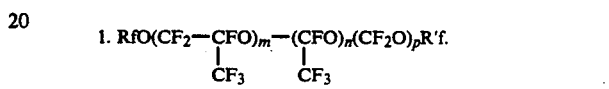

(Rf, R'f, like or different from each other, are the same as defined for the products of formula (I);

2. RfO(CF$_2$CF$_2$O)$_n$(CF$_2$O)$_p$R'f where Rf and R'f are the same as defined for the products of formula (I), excluding the value of —C$_3$F$_7$;

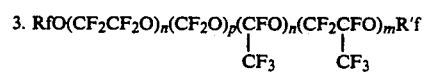

where Rf and R'f have the meaning illustrated for the products of formula (I);

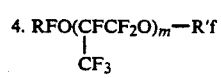

in which Rf and R'f have the meaning illustrated for the products of formula (I), excluding the value of —CF$_3$;

5. RfO(CF$_2$CF$_2$O)$_r$—R'f in which Rf and R'f have the value illustrated for the products of formula (I), excluding the value of C$_3$F$_7$;

6. RfO(CF$_2$CF$_2$CF$_2$O)$_r$—R'f where Rf and R'f have the meaning illustrated for the products of formula (I).

Polyfluoropolyoxyalkylenes which are utilizable for the compositions of the invention are also the ones having structure:

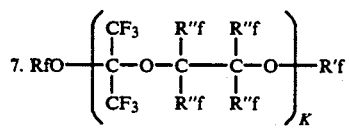

in which Rf and R'f have the value illustrated for the products of formula (I) and R"f can be F or a perfluoroalkyl group.

In the polyperfluoropolyoxyalkylenes of classes 1 to 7 illustrated above, the values of m, n, p, q, r and K are such as to satisfy an average molecular weight of the perfluoropolyether ranging from 500 to 15,000.

Lastly, among the cyclic polyfluoropolyoxyalkylenes of formula (II), the ones of formula:

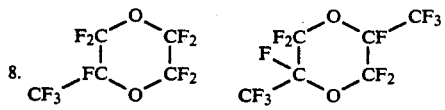

are cited in particular.

When Rf and R'f are perfluoroalkyl groups, the perfluoropolyoxyalkylenes of classes (1) and (8) are known under the trade name—Fomblin ® Y or Galden ®; the ones of class (2) are known under the trade name Fomblin ® Z, all of them being produced by Montedison S.p.A. The products of class (4) are known under the trade name Krytox ® and are produced by DuPont; the products of class (5) are described in U.S. Pat. No. 4,523,039 or in J. Am. Soc. 1985, 107, 1197–1201. The products of class (6) are described in European patent No. 148,482 to Daikin; the products of class (3) are preparable according to U.S. Pat. No. 3,665,041; the products of class (7) are described in PCT patent application WO.87/0538.

The compositions forming one of the objects of the present invention preferably contain from 0.01 to 3%, and more preferably from 0.02 to 0.08% by weight, calculated on the composition, position, of the above-described dyestuffs. Said compositions are utilizable in all the applications which are known for the perfluoropolyoxyalkylenes, and in particular in those where their coloration results of advantage such as in thermometers, pressure-gauges and other visual measuring instruments, and also as tracing means in porous materials.

The following examples are given to illustrate the present invention, without limiting however the scope thereof.

EXAMPLE 1

10 g of Neutral Red (C.I. 50,040) having formula:

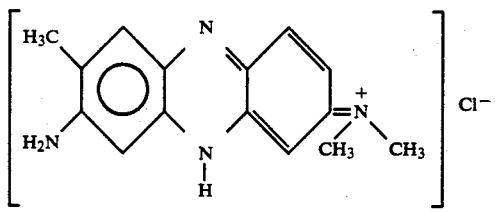

were treated with 100 cm³ of an aqueous ammonia solution at 5%, thereby obtaining the precipitation of the corresponding base.

It was filtered, washed with distilled water until negative reaction of the chlorides in the washing waters, and then it was dried at 30°–40° C. in air.

The resulting product was dispersed along with 28 g of a perfluoropolyoxyalkylene compound of formula:

having an average molecular weight equal to 800 and a m/n ratio=6, in 1000 cm³ of 1,1,2-trichloro-1,2,2-trifluoroethane. It was reacted for 2 hours.

On conclusion of the reaction, the I.R. analysis of the solution revealed traces of free —COOH groups.

The solution so obtained was filtered on a polytetrafluoroethylene membrane having pores of 0.45μ, under pressure, and it was evaporated to dryness, thereby obtaining, as a residue, the red-violet dyestuff of formula:

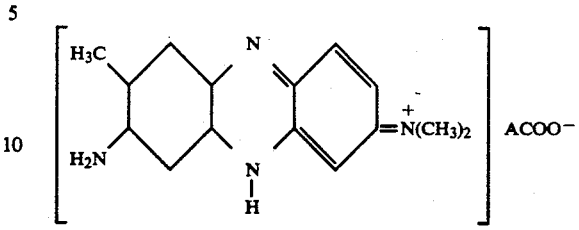

where A is the perfluorooxyalkylene chain.

This dyestuff was dissolved, in an amount equal to 0.03% by weight, in a perfluoropolyoxyalkylene of the above illustrated class (1), having an average molecular weight of about 800, with values of $$\frac{m}{n+p} = 5 \text{ and } \frac{n}{p} = 2$$

A slightly fluorescent, Magenta red solution was so obtained.

EXAMPLE 2

1-amino-4-chloroanthraquinone was reacted with a molar defect of the potassium alcoholate of formula:

$$CF_3O(CF_2O)_m(CF_2CFO)_n-CF_2-CH_2-OCH_2CH_2OK$$
$$|$$
$$CF_3$$

having an average molecular weight equal to 850, with a m/n value equal to 5.

Said alcoholate can been obtained from the corresponding alcohol by reaction with potassium t-butylate in the presence of diglyme (diethylene glycol dimethylether) as a dispersant, at 70° C.

After a 2-hour reaction, the obtained product was discharged from the reactor, it was washed with water and extracted with Freon ®, thereby obtaining a wax-like violet residue.

Such product was dissolved in the perfluoropolyoxyalkylene of example 1, in an amount equal to 0.01% by weight, to provide a violet colored solution.

EXAMPLE 3

55 g of the acid of formula:

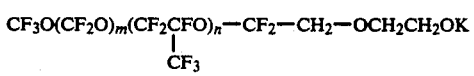

having an average molecular weight equal to 3,000 and a m/n ratio=25, were reacted with 15 ml of SOCl₂ at 70°–80° C. in the presence of 0.5 ml of pyridine.

On conclusion of the gas evolvement (HCl, SO₂) it was evaporated to dryness in order to remove SOCl₂ and on the resulting product the presence of end group

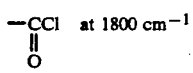

was determined by means of I.R. analysis.

To such product, 10.5 g of 1-aminoanthraquinone were added, the mixture was brought to 100° C. and was maintained at this temperature for 3 hours under stirring.

Then it was cooled and evaporated to dryness, it was extracted with 1,1,2-trichloro-1,2,2-trifluoroethane, obtaining, after filtration, about 50 g of a very viscous, gold yellow oil, which, on I.R. analysis, exhibited the band at 1740 cm$^{-1}$ typical of an amide of formula:

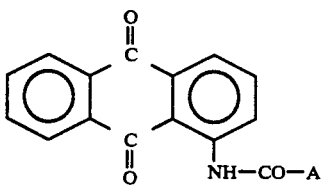

where A is the perfluoropolyoxyalkylene chain of formula:

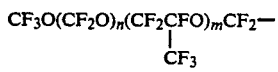

Such amide is soluble in Galden D05 and imparts to it a yellow color. This color is stable also to heating to 170° C.

EXAMPLE 4

The dyestuff prepared in the preceding example was added in an amount of 1% to a polyfluoropolyoxyalkylene of formula:

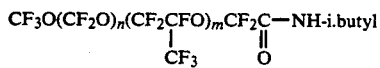

having an average molecular weight equal to 5,000 and a m/n ratio equal to about 25.

A yellow solution was obtained.

Such solution, applied onto a porous concrete surface, permits to follow the penetration rate and degree of perfluoropolyoxyalkylene inside the material.

EXAMPLE 5

12 g of 1-aminoanthraquinone were reacted at 100° C. with 30 g of an acyl fluoride of formula:

FOC—CF$_2$O(CF$_2$CF$_2$O)$_m$(CF$_2$O)$_n$CF$_2$COF having an average molecular weight of 4,000 and a m/n ratio equal to 0.8.

After a 4-hour reaction, it was cooled, it was extracted with 1,1,2-trichloro-1,2,2-trifluoroethane and it was filtered, and the solvent was removed from the extract by evaporation to dryness.

The residue, subjected to I.R. analysis, resulted to be an amide of formula:

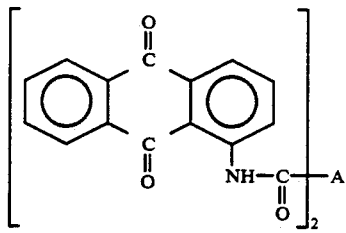

with absorption at 1740 cm$^{-1}$ by the group

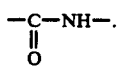

The product, exhibiting a yellow color, was added in an amount of 0.8% by weight to Galden D10 and to Fomblin Y25, in which it dissolved imparting a yellow color to the solution.

EXAMPLE 6

3 g of malachite green were treated with aqueous ammonia in excess, thereby causing the precipitation of the free base:

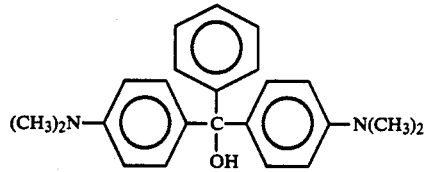

It was filtered and the residue was dried at 60° C. under vacuum. After cooling, such residue was additioned with 100 ml of 1,1,2-trichloro-1,2,2-trifluoroethane, whereafter there were added 10.4 g of an acid having formula:

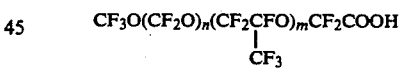

having a m/n ratio equal to 5 and an average molecular weight equal to 800.

After stirring for 2 hours at room temperature, the solution was brought to dryness by removing the chlorofluorinated solvent, so obtaining, as a residue, a blue colored product which, on I.R. analysis and NMR analysis, exhibited the formula:

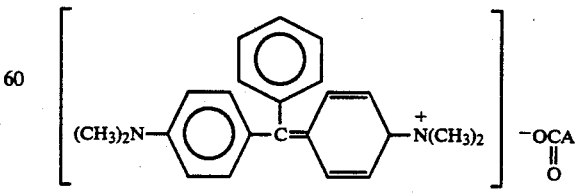

Such product dissolved in HT(®)70 or in Galden(®) D05 or in Fomblin(®)Y25 in amounts of 0.05%, imparting a blue color to said products.

EXAMPLE 7

20 g of Crystal Violet (C. I. 42555) of formula:

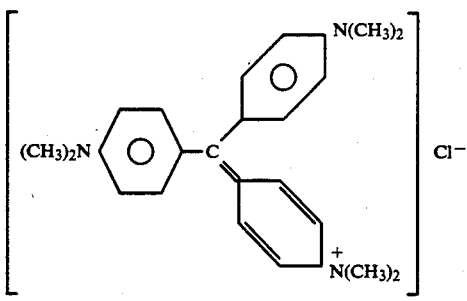

were treated with an aqueous ammonium hydrate solution in order to precipitate the free base (C.I. 42555:1).

After filtration, the residue was dried at 40°-50° C. under vacuum and was treated with about 50 g of the same acid having a perfluoropolyoxyalkylene chain described in example 1, and 1,500 ml of 1,1,2-trichloro-1,2,2-trifluoroethane. After a 2-hour stirring, the solvent was distilled under vacuum.

The residue, consisting of the dyestuff of formula

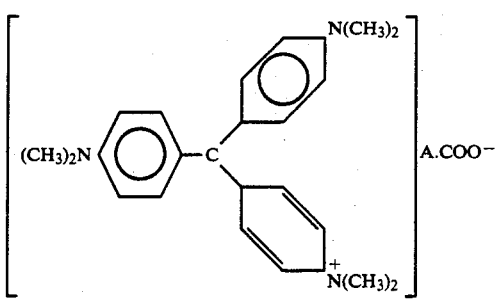

was dissolved in an amount of 0.06% in polyfluoropolyoxyalkylenes such as, for example, Galden D 05 and Fomblin Y 25, to which it imparted a blue-violet color.

We claim:

1. A dyestuff for polyfluoropolyoxyalkylenes, said dyestuff having the formula:

Q[B—(A)$_s$]$_t$ or [(Q)$_s$—B]$_2$A wherein:

Q is selected from the group consisting of azo, stilbene, diphenylmethane, triarylmethane, xanthen, acridine, quinoline, methine, polymethine, indamine, indophenol, azinic, oxazine, thiazine, and anthraquinone dyestuffs;

A is a perfluoroxyalkylene polymer chain having perfluoroxyalkylene units having the formulas:

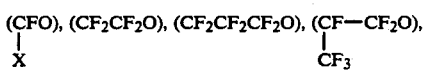

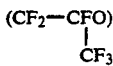

where X=F or CF$_3$, said perfluorooxyalkylene polymer chain having the formula:

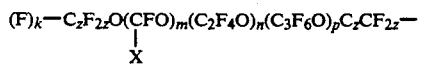

wherein said units are randomly arranged and wherein z=an integer from 1 to 3;

m, n and p=integers ranging from 0 to 50, the sum of which is at least 2;

k=1 when said dyestuff has the formula Q[B—(A)$_s$]$_t$ and 0 when said dyestuff has the formula [(Q)$_s$—B]$_2$A, the average molecular weight of A ranging from 500 to 15,000;

B is an organic group which is at least divalent;

t=1 or 2;

s=1 or 2.

2. The dyestuff of claim 1, wherein B is selected from the group consisting of:

—O—CH$_2$—;

—(OCH$_2$CH$_2$)$_n$OCH$_2$;

—CH$_2$OCH$_2$—;

—S—CH$_2$—CH$_2$OCH$_2$;

—CH$_2$OCH$_2$OCH$_2$—;

—CH$_2$OCH$_2$CH$_2$OCH$_2$—;

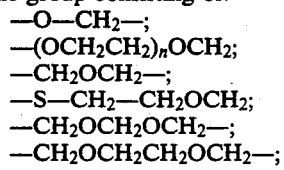, wherein R$_a$ = an alkyl containing 1 to 3 carbon atoms;

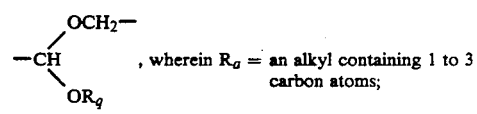

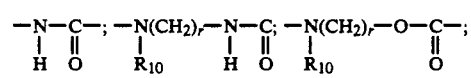

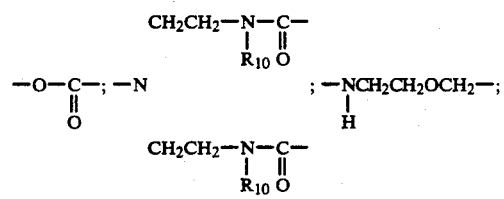

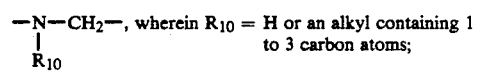

—N—CH$_2$—, wherein R$_{10}$ = H or an alkyl containing 1 to 3 carbon atoms;
|
R$_{10}$

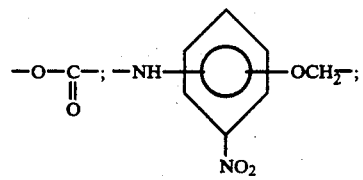

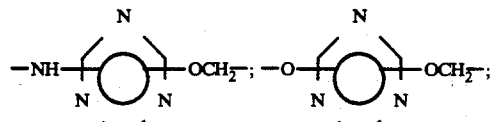

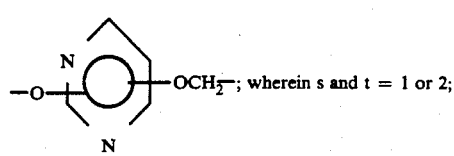; wherein s and t = 1 or 2;

r = 1, 2 or 3; N = a number from 2 to 6;

with the proviso that when B is —O—C—,
                                     ||
                                     O Q has a positive charge and is bound to the —O—C—
                                              ||
                                              O
group through an ionic bond.

3. A composition comprising:
(a) the dyestuff of claim 1; and
(b) a polyfluoropolyoxyalkylene, said polyfluoropolyoxyalkylene having the formula:

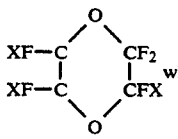
wherein X = F or CF₃; or the formula

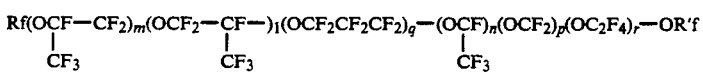

where having randomly distributed perfluorooxyalkylene units having the formulas:

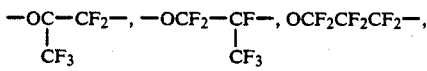

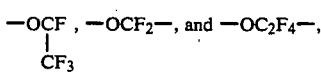

Rf and R'f, like or different from each other, are perfluoroalkyl radicals containing 1 to 3 carbon atoms, or groups having the formula —CFCL, wherein X=F or CF₃, and L is a functional organic radical having the formula

—COR₁ in which R₁ is a radical —OR₂ or —NR₂R₃, where R₂=H or an alkyl containing 1 to 16 carbon atoms; R₃ is equal to R₂, or is a radical selected from the group consisting of —CH₂CH₂OH, —(CH₂CH₂O)$_n$H, wherein n ranges from 2 to 6; —(CH₂)₃Si(OR₈)₃, wherein R₈=—CH₃ or —C₂H₂; —CH₂—CH=CH₂; phenyl;

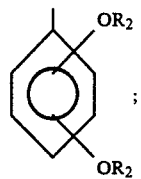

and a heterocyclic radical; or L has the formula

—CH₂R₄ in which R₄ is a radical —OR₅ or —NR₅R₆, wherein R₅ and R₆, like or different from each other, are selected from the group consisting of H, —CH₂CH₂OH;

—CH₂—CH—CH₂;
      |    |
      OH  OH

—(CH₂CH₂O)$_n$H, wherein n ranges from 2 to 6;

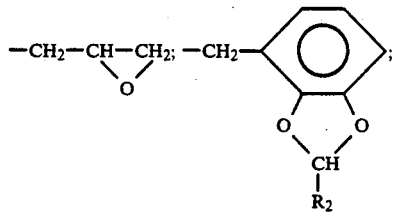

CH₂CH₂CH₂Si(OR₈)₃;

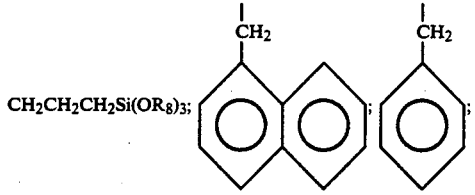

and a heterocyclic radical, wherein R₂ and R₈ have the same meaning as defined above; l, m, n, p, q, r are numbers ranging from 0 to 50, the sum m+n+p+q+r being at least 2.

* * * * *